United States Patent
Chiang et al.

(10) Patent No.: US 9,421,235 B2
(45) Date of Patent: Aug. 23, 2016

(54) **MEDICINE CONTAINING EXTRACTS OF *FICUS MICROCARPA* FOR HEALING WOUNDS OF A DIABETIC PATIENT**

(75) Inventors: Shou-Hsun Chiang, Chiayi (TW); Chun-Tw Wang, Chiayi (TW); Li-Yi Huang, Chiayi (TW)

(73) Assignee: Shou-Hsun Chiang, Chiayi (TW)

( * ) Notice: Subject to any disclaimer, the term of this patent is extended or adjusted under 35 U.S.C. 154(b) by 0 days.

(21) Appl. No.: 13/556,231

(22) Filed: Jul. 24, 2012

(65) Prior Publication Data

US 2013/0052289 A1 Feb. 28, 2013

(30) Foreign Application Priority Data

Aug. 22, 2011 (TW) .............................. 100130004 A

(51) Int. Cl.
*A61K 36/60* (2006.01)

(52) U.S. Cl.
CPC ..................................... *A61K 36/60* (2013.01)

(58) Field of Classification Search
None
See application file for complete search history.

(56) References Cited

PUBLICATIONS

Ao et al., Evaluation of antioxidant and antibacterial activities of Ficus microcarpa L. fil. extract, 2008, Food Control, 19: 940-948.*

* cited by examiner

*Primary Examiner* — Terry A McKelvey
*Assistant Examiner* — Catheryne Chen
(74) *Attorney, Agent, or Firm* — Raymond Y. Chan; David and Raymond Patent Firm

(57) ABSTRACT

A medicine containing extracts of *Ficus microcarpa* for healing wounds including ulcerous wounds of a diabetic patient is provided. In one embodiment, the medicine is ointment, fluid, or spray for skin application. In another embodiment, the medicine is pill, powder, ointment, fluid, spray, tablet, or capsule for oral administration. In still another embodiment, the medicine is implemented as fluid for injection.

3 Claims, 3 Drawing Sheets

MEDICINE CONTAINING EXTRACTS OF FICUS MICROCARPA FOR HEALING WOUNDS OF A DIABETIC PATIENT

BACKGROUND OF THE INVENTION

1. Field of the Invention

The invention relates to the promotion of wound healing and more particularly to a medicine containing an extract of Ficus microcarpa for healing wounds concerning cuts, scrapes, or breaks in skins.

2. Description of Related Art

Ficus microcarpa is an evergreen tree grown widely in southern China and Taiwan. According to classical and folk medicinal herbs, all parts of Ficus microcarpa can be used as medicines to improve blood flow, reduce blood stasis, cure fever, and expel dampness accumulated in the body. Also, they can heal bruising due to impacts, chronic bronchitis, flu, pertussis, tonsillitis, bacillary dysentery, enteritis, red eye, and toothache. According to a traditional Chinese medicine record, Ficus microcarpa can eliminate sores in the bones, eliminate bruising on the body, relieve pain, and it can be soaked in wine to cure various diseases. According to a second traditional Chinese medicine record, Ficus microcarpa can treat broken bones, eliminate swelling, relieve pain, eliminate bruising due to impacts, and treat broken bones and muscles. According to a third traditional Chinese medicine record, Ficus microcarpa can cure dysentery. According to a fourth traditional Chinese medicine record, Ficus microcarpa can cure fever and expel dampness accumulated in body. According to a fifth traditional Chinese medicine record, Ficus microcarpa can cure heatstroke, diminish inflammation, and diminish cough. It also can cure big heat, typhoid due to sexual activity, nosebleed, throat swelling, tonsillitis, conjunctivitis, malaria, pertussis, bruising and swelling due to impacts, muscle damage, and relieve muscle pain. In addition, the fruits of Ficus microcarpa can cure carbuncles and ulcers, and the latex of Ficus microcarpa can cure pannus on eye, red eye, carbuncle on lip, and psoriasis.

Currently, although there are some products using the aerial roots and leaves of Ficus microcarpa to cure cough, cold, asthma, chronic bronchitis, a report on healing wounds using Ficus microcarpa is not yet found. Hence, the invention is neither taught nor rendered obvious thereby.

SUMMARY OF THE INVENTION

It is therefore one object of the invention to provide a medicine containing an extract of Ficus microcarpa for healing wounds concerning cuts, scrapes, or breaks in skins.

The above and other objects, features and advantages of the invention will become apparent from the following detailed description taken with the accompanying drawings.

DETAILED DESCRIPTION OF THE INVENTION

Term Definitions

"Wound" means an injury concerning a cut, a scrape or a break in the skin, which is caused by a knife or other objects.

"Promotion, promoted, or promoting" means a gradual healing of the wound.

"Patient" means one of mammals suffering illness. Specifically, the mammal is human being.

"Carrier" means diluent or excipient in the field of medications.

"Raw material" means portions of Ficus microcarpa above the ground, which include leaves (1-100 wt %), aerial roots (1-100 wt %), branches (1-100 wt %), and fruits (1-100 wt %), being cut and dried prior to extraction.

"Medicine containing an extract of Ficus microcarpa" means medicine being obtained by boiling the raw material in water, so that the extract contains various ingredients of the raw material that assist in healing wounds.

A method of extracting Ficus microcarpa of the invention comprises the steps of cutting portions of Ficus microcarpa, which include leaves, aerial roots, branches and fruits, above the ground, drying the leaves, aerial roots, branches and fruits of Ficus microcarpa as raw material, and boiling the raw material in water to obtain a concentrated solution, whereby the concentrated solution contains an extract including various ingredients from the raw material that assist in healing wounds.

A medicine for healing wounds according to the invention comprises an extract of Ficus microcarpa, wherein the amount of the extract occupies at least 1% of the medicine by weight.

The medicine can be applied to a skin wound by spraying or other method. For spraying method, the medicine can be made by mixing the extract with a liquid carrier. Alternatively, the medicine can be made in solid form by mixing the extract with a solid carrier or the medicine can be made in semisolid form by mixing the extract with a semisolid carrier. For medicine of semisolid form, the semisolid carrier has a dynamic viscosity greater than water. End product can be gel, lotion, emulsion, cream, ointment, or foam. The end product can be obtained by mixing the extract with a carrier, which mainly serves as a stabilizing or wetting or diluting agent, and the end product can be sterilized if required. Preferably, the end product of the invention is cream. Preferably, the carrier may include fatty acid, wax, grease, alcohol, and synthetic fat. The medicine of the invention can be further combined with emollients, aroma, or pigments so as to be more acceptable to people.

A bandage impregnated with the medicine of the invention in which the medicine comprises an extract of Ficus microcarpa for healing wounds concerning cuts, scrapes or breaks in skins. The bandage can be a gauze, compression, triangular, or tube bandage.

The medicine of the invention can be made into, but not limited to, pill, powder, ointment, fluid, spray, tablet, or capsule by mixing the extract with a carrier, which serves as a diluent or a excipient in the field of medications. If required, the medicine can be sterilized.

Figure 1:
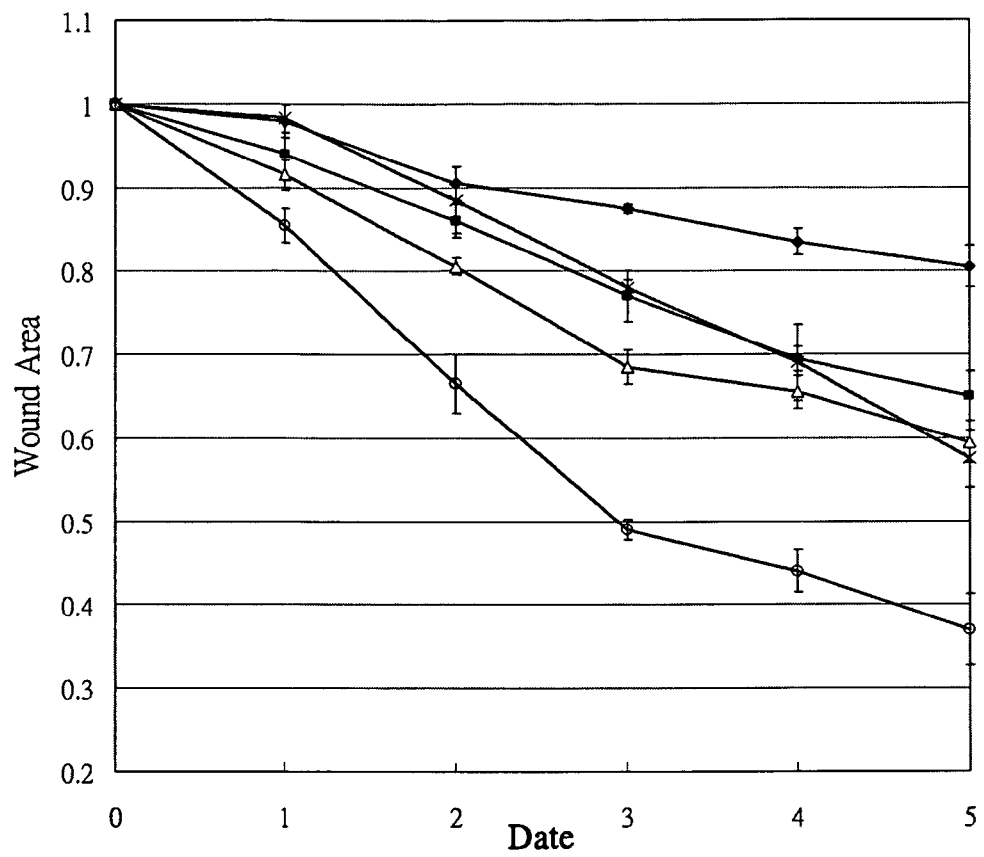
FIG. 1 plots wound area versus day for showing results of experiments performed on five groups of mice to prove the effectiveness of the medicine of the present invention in healing wounds.
Figure 2:
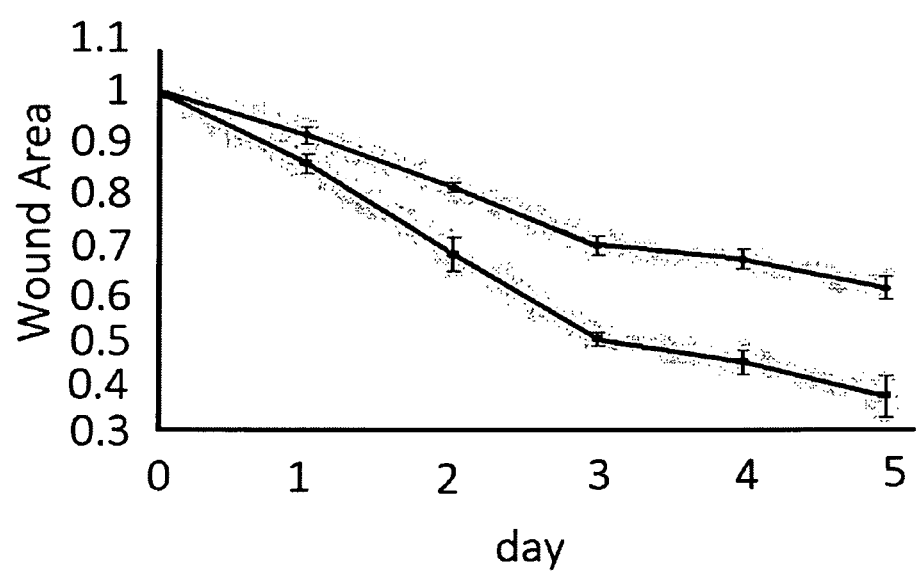
FIG. 2 plots wound area versus day for showing results of experiments performed on the topical application group and the dual application group to prove additional oral medicine given to the mice can increase the healing effect on the wounds.
Figure 3:
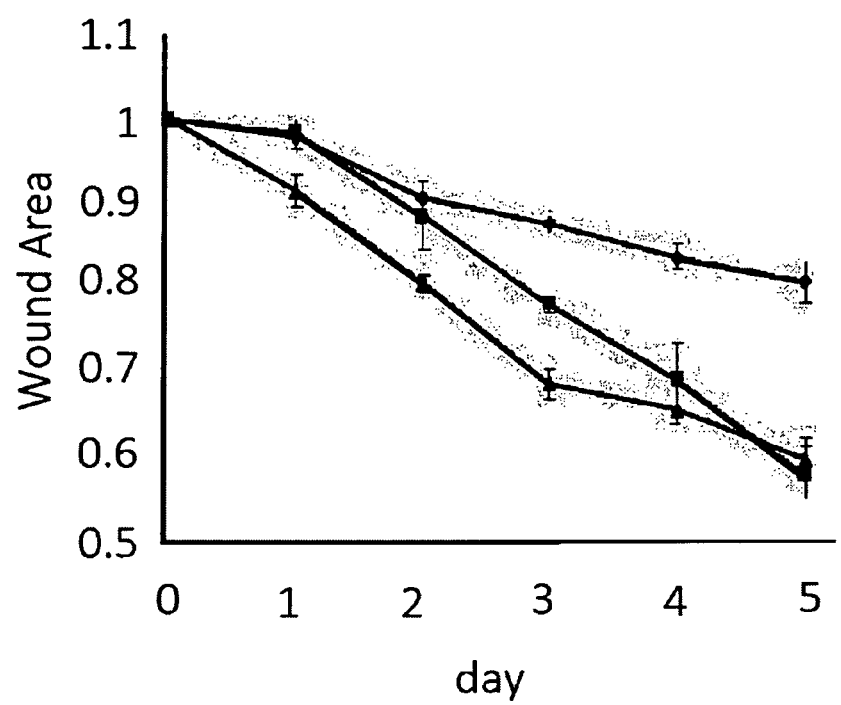
FIG. 3 plots wound area versus day for showing results of experiments performed on the control group, the oral application group, and the topical application group to prove that either of the oral medicine and the topical medicine of the present invention can be used to heal wounds.

Referring to FIGS. 1 through 3, a medicine containing an extract of *Ficus microcarpa* for healing wounds concerning cuts, scrapes or breaks in skins in accordance with the invention will be discussed in detail below.

In a first preferred embodiment, the medicine of the invention can be obtained by adding 8,000 cc water to a still pot containing 100 g raw material, heating the still pot at 100° C. for about three hours to obtain a concentrated solution containing various ingredients of the raw material, taking the concentrated solution out of the still pot when the ratio of the raw material to the concentrated solution reaches 1:7.5, mixing the concentrated solution with a carrier (serving as a excipient), wherein the ratio of the concentrated solution to the carrier is about 4:1, to obtain a semisolid form of medicine, stirring the semisolid form of medicine, and dividing the semisolid form of medicine into several flasks and putting the flasks in a refrigerator which is kept at 4° C.

In a second preferred embodiment, a medicine of the invention can be obtained by adding 8,000 cc water to a still pot containing 100 g raw material, heating the still pot at 100° C. for about three hours to make a concentrated solution containing various ingredients of the raw material, and taking the concentrated solution out of the still pot when the ratio of the raw material to the concentrated solution reaches 1:50. The concentrated solution can be used as medicine directly.

The medicine of the invention can be made in an oral form (to be taken by mouth) or a topical form (to be applied to skin). To have a better effect, a patient having a skin injury can take the oral medicine and the topical medicine during the treatment period. Dose of the medicine to be administered depends on property, condition, age and health condition of a patient, the way of taking medicine, and other information about therapy. Also, the way of taking medicine, either via mouth or skin, depends on age of a patient, weight of the patient, health condition of the patient, etc.

In a third preferred embodiment, wound healing on a skin wound area of a mouse is performed using the medicine of the invention. To prove the healing effects of the medicine of the present invention, mice with skin wounds are experimented. In detail, mice are divided into five groups, including a control group, an excipient application group (the mice of this group are given the excipient that does not contain the extract of the medicine), an oral application group (the mice of this group are given the medicine of oral form), a topical application group (the mice of this group are given the medicine of topical form), and dual application group (the mice of this group are given both the medicine of oral form and the medicine of topical form) in which each group has 6 mice labeled C57BU6J and each mouse has a weight of about 21 to 25 g. Each mouse is anesthetized first. Next, the hair on the back of the mouse is removed by clipping, thereby leaving a bare skin area. Iodine is applied to the bare skin area for disinfection purpose. Remove the skin and its surrounding tissues using a surgical knife (i.e., causing a skin wound).

No medicine is applied to the mice of the control group but gauze is put on the bare skin for preventing infection. Each mouse of the excipient application group is applied with an excipient that does not contain the extract of the medicine of the present invention.

Medicine of topical form is applied to the skin wound area of each mouse of the topical application group once per 24 hours. Medicine of oral form is fed into the mouth of each mouse of the oral application group a number of times per day, the total amount of the medicine being fed is 3 g per day. Both the medicine of oral form and the medicine of topical form are performed on each mouse of the dual application group respectively at the same amount of medicine used in the oral application group and the topical application group.

The skin wound area for each mouse is recorded on each day of the following five days for evaluating the healing effects of the medicine.

Results of the above experiments are detailed below. As shown in FIG. 1, compared with the control group and the excipient application group, the oral application group, the topical application group, and the dual application group have a better healing effect on skin wounds. It is proved that the medicine of the present invention can promote the healing effect on skin wounds.

In FIG. 1, character "♦" represents the control group, character "□" represents the excipient application group, character "Δ" represents the topical application group, character "×" represents the oral application group, and character "○" represents the dual application group.

FIG. 1 shows that the excipient application group has a healing effect better than the control group. The reason is that the excipient applied to the excipient application group can provide an occlusive barrier to prevent extensive scabbing.

In FIG. 2, character "♦" represents the topical application group and character "□" represents the dual application group.—

In FIG. 3, character "♦" represents the control group, character "□" represents the oral application group, and character "▲" represents the topical application group.

FIG. 2 shows that the dual application group, where each mouse is given both the oral medicine and the topical medicine during the treatment period, has a best healing effect on skin wounds. As shown, with additional oral medicine, the healing effect on skin wounds can be increased significantly.

FIG. 3 shows that either of the topical medicine and the oral medicine can provide a healing effect on skin wounds While the invention has been described in terms of preferred embodiments, those skilled in the art will recognize that the invention can be practiced with modifications within the spirit and scope of the appended claims.

What is claimed is:

1. A medicine for healing wound of a patient to heal knife wound, burn, frostbite, ulcerous wound of the patient, comprising:
   an extract of raw material of *Ficus microcarpa* containing dried leaves, dried aerial roots, dried branches and dried fruits of *Ficus microcarpa*;
   a shaping agent mixed with said extract to form a viscous formed medicine for applying on the wound area of the patient;
   a carrier mixed with said extract and said shaping agent for inhibiting growth of microorganisms on the wound area of the patient; and
   a bandage, wherein said viscous formed medicine is impregnated on said bandage for directly applying on the wounded area of the patient.

2. A medicine for healing wound of a patient to heal knife wound, burn, frostbite, ulcerous wound of the patient, comprising:
   an extract of raw material of *Ficus microcarpa* containing dried leaves, dried aerial roots, dried branches and dried fruits of *Ficus microcarpa*;
   a shaping agent mixed with said extract to form a viscous formed medicine for applying on the wound area of the patient, wherein said viscous formed medicine is selected from the group consisting gel, lotion, emulsion, cream, ointment, and foam for applying on the wound area of the patient;
a carrier mixed with said extract and said shaping agent for inhibiting growth of microorganisms on the wound area of the patient, wherein said carrier is selected from the group consisting of sedative and moisture agent; and
a bandage, wherein said viscous formed medicine is impregnated on said bandage for directly applying on the wounded area of the patient.

3. A medicine for healing wound of a patient to heal knife wound, burn, frostbite, ulcerous wound of the patient, comprising:
an extract of raw material of *Ficus microcarpa* containing dried leaves, dried aerial roots, dried branches and dried fruits of *Ficus microcarpa*;
a shaping agent mixed with said extract to form a viscous formed medicine for applying on the wound area of the patient; and
a carrier mixed with said extract and said shaping agent for inhibiting growth of microorganisms on the wound area of the patient;
wherein said medicine is made in a solid form selected from the group consisting of pill, powder, tablet and capsule as an oral medicine.

\* \* \* \* \*